(12) United States Patent
Voss et al.

(10) Patent No.: US 6,375,611 B1
(45) Date of Patent: Apr. 23, 2002

(54) ORGAN STABILIZER

(75) Inventors: Larry Voss, San Jose; Steven Peng, Burlingame; David Hancock; Grace Carlson, both of San Francisco, all of CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 09/479,358

(22) Filed: Jan. 7, 2000

(51) Int. Cl.$^7$ ................................................ A61B 1/32
(52) U.S. Cl. ........................... 600/210; 600/235; 600/37
(58) Field of Search ................................. 600/201, 203, 600/210, 227, 228, 229, 231, 232, 235, 37

(56) References Cited

U.S. PATENT DOCUMENTS

| | | | |
|---|---|---|---|
| 5,865,730 A | 2/1999 | Fox et al. | 600/228 |
| 6,019,722 A * | 2/2000 | Spence et al. | 600/235 X |
| 6,036,641 A * | 3/2000 | Taylor et al. | 600/235 X |
| 6,063,021 A * | 5/2000 | Hossain et al. | 600/37 |
| 6,071,235 A * | 6/2000 | Furnish et al. | 600/201 X |
| 6,152,874 A * | 11/2000 | Looney et al. | 600/214 |

FOREIGN PATENT DOCUMENTS

WO 97/40738 * 11/1997

* cited by examiner

*Primary Examiner*—Jeffrey A. Smith
(74) *Attorney, Agent, or Firm*—Fenwick & West, LLP

(57) ABSTRACT

An organ-stabilizing element is covered with a layer of textile material such as cloth enhance slip-free engagement with an organ such as a beating heart during surgery thereon. The organ-stabilizing element is supported on a stacked structure of successive ball elements and rings that can be selectively flexible or rigid in response to tensioning of a flexible cable within a central bore of the structure.

4 Claims, 5 Drawing Sheets

ORGAN STABILIZER

FIELD OF THE INVENTION

This invention relates to surgery methods and apparatus, and more particularly to apparatus for stabilizing a portion of the surface of an organ (e.g., a beating heart) during surgery thereon, and to a method for enhancing effective engagement of the stabilizing apparatus with surface tissue of the organ.

BACKGROUND OF THE INVENTION

Contemporary cardiac and cardiovascular surgical procedures endeavor to accomplish the intended surgical intervention with minimum invasiveness and trauma in order to promote more rapid healing with minimum recuperative discomfort and complications. With improvements in skill and knowledge and surgical instrumentation, many more cardiac and cardiovascular procedures are being successfully achieved while the heart continues to beat, thus obviating complications and increased costs and complexity of transferring a patient to dependence upon a cardiopulmonary bypass machine while the heart is immobilized. Thus, so-called beating-heart surgical procedures on patients are favored where possible, but are nevertheless associated with other difficulties attributable to the dynamics of the continuously moving heart, and with the slippery moist surface of the heart. Various techniques have been attempted to stabilize the heart including applying a suction stabilizer, and installing temporary sutures positioned in tension about target sections of the beating heart. Such techniques are not always reliable in many surgical situations. Another technique to stabilize the heart includes contacting the heart with a fork-like member. However, low coefficient of friction between the moist surface of the heart and the contacting member requires greater normal force to be applied against the surface of the heart to attain adequate stabilization. This results in deformation of the heart chambers which can lead to lowered pumping efficiency and possible arrhythmia. Also, greater normal force applied to the heart can puncture or scrape the heart wall. Accordingly, it would be desirable to provide heart stabilizing apparatus and method for reliable positioning in contact with a beating heart to stabilize at least target sections of the heart during a surgical procedure, using a minimum of normal force applied to the heart via a compliant surface to inhibit perforation or tissue damage, and without causing hematomas in compressed tissue and without significantly interfering with rhythmic beating of the heart muscles.

SUMMARY OF THE INVENTION

In accordance with the illustrated embodiment of the present invention, a stabilizing mechanism is mounted on a flexible structure that can be conveniently manipulated to facilitate positioning the stabilizing mechanism in contact with an organ such as a beating heart, and that can then be selectively made rigid relative to a support frame in order to provide rigid support where positioned on the beating heart. The portion of the stabilizing mechanism that is disposed to contact the heart is covered with a textile material (preferably an absorbent material) to promote improved engagement with the external surface of the heart without significant slippage. And, the textile material contributes cushioning or padding to inhibit tissue damage at the contact locations on the external surfaces of the organ such as a beating heart.

DETAILED DESCRIPTION OF THE INVENTION

Figure 1:
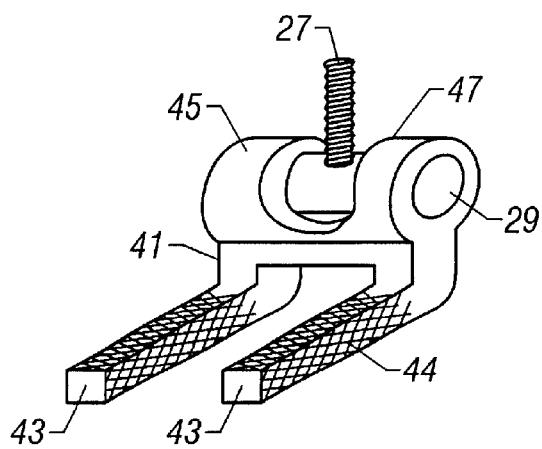
FIG. 1 is a perspective view of a fork-like embodiment of the supporting element according to the present invention for attachment to the distal end of the structure of FIG. 4.
Figure 4:
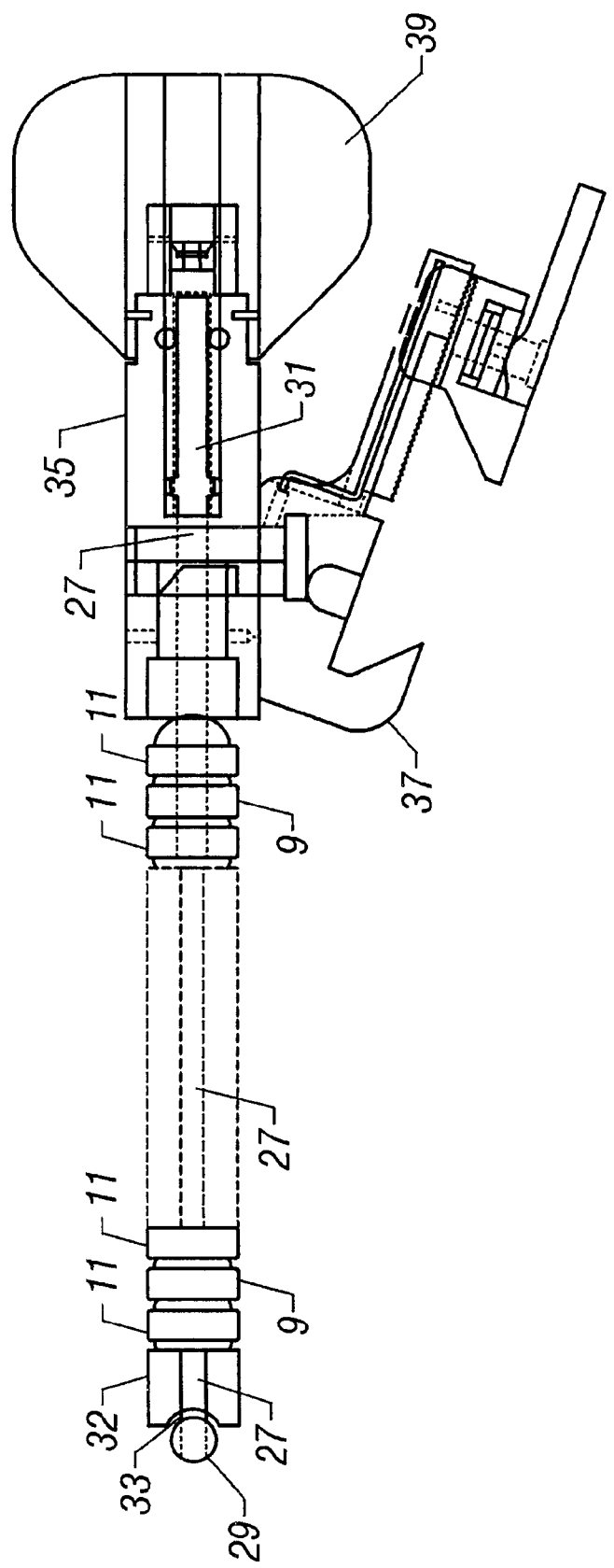
FIG. 4 is a pictorial illustration of the stacked structure of FIG. 3 including proximal and distal end members to complete the supporting structure for the supporting element that contacts a heart.

Referring now to the perspective view of FIG. 1, there is shown a fork-like element 41 having a pair of tines 43 attached to a cylindrical component 45 that traverses the spacing between tines 43. This element 41 is disposed to fit against a yoke-like end element 32 within a lateral groove 33 therein, as described later herein and as illustrated in FIG. 4, and includes the lateral bar 29 at the distal end of a cable 27 within the cylindrical component 45. A circumferential slot 47 intermediate the ends of the cylindrical component 45 facilitates rotation through a significant angle of the fork-like element 41 around the axis of the lateral bar 29 without interference from cable 27.

In accordance with one embodiment of the present invention, the tines 43, or other supporting shape, are covered with a textile material 44 such as woven or non-woven fabric at least on the surfaces thereof disposed to contact the beating heart, or other organ. The tines 43 may be so covered to a thickness of such material generally within a range of about 0.015 inches to about 0.064 inches, although additional thickness of the textile material 44 may also be useful as providing additional cushioning against tissue damage upon contact with the surface of the heart. In one embodiment, non-woven rayon fibers are used as the textile material 44 to promote enhanced friction, or at least slip-free engagement, with the surface of the heart, believed to be attributable in part to absorptive characteristics of a textile material 44 that diminishes the volume of lubricious liquid on the surface of the heart in contact with the material. In another embodiment, non-woven or woven cotton fabric may cover the tines 43 to within the limits of thickness described above, but care in the treatment of such fabric is required to reduce the incidence of shedding lint or loose fibers in the surgical environment about the heart. The textile material 44 may be held in place on the tines 43, for example, by using a bioinert adhesive such as commerciallyavailable Loctite 4013 adhesive or by welding the textile to the fines. Enhanced slip-free engagement of the textile-covered tines 43 with the surface of the heart is also believed to be due in part to the surface roughness of the textile covering which promotes minute conformal deformation of surface tissue into mating engagement with the surface topology of the textile material 44. Thus, the characteristics of the textile material 44 may be selected within the constraints described above for absorptiveness, substantially lint-free service, and surface roughness.

Figure 7:
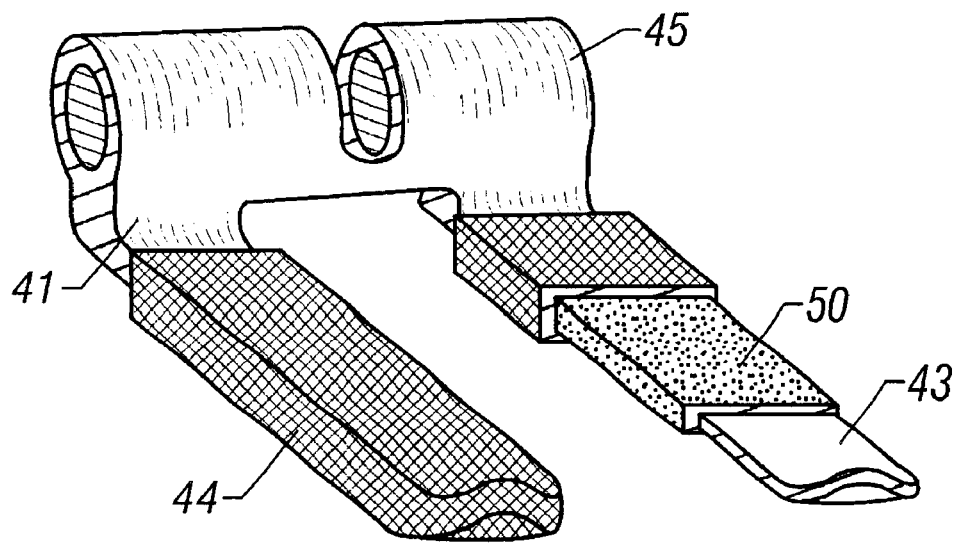
FIG. 7 is a pictorial illustration of the fork-like embodiment of the supporting element with cut-away views of the textile and compliant materials.

In an alternative embodiment, as shown in FIG. 7, a layer 50 of compliant material such as foamed polyurethane is disposed between the textile material 44 and the rigid tines 43 of the element 41. The foamed polyurethane layer 50 provides compliant medium to soften or cushion the contact with the heart and conform to the surface of the heart to provide greater surface area of contact, thereby to distribute the contacting force over greater contact area to reduce tissue damage and the possibility of puncturing the heart. The layer 50 of compliant material may be an absorptive foam material disposed between the tines 43 and the textile material 44 to facilitate drying the surface of a heart or other organ being contacted, thereby to improve the coefficient of friction between the surface of the heart, or other organ, and the textile material 44 covering the tines 43 of the element 41.

Figure 8:
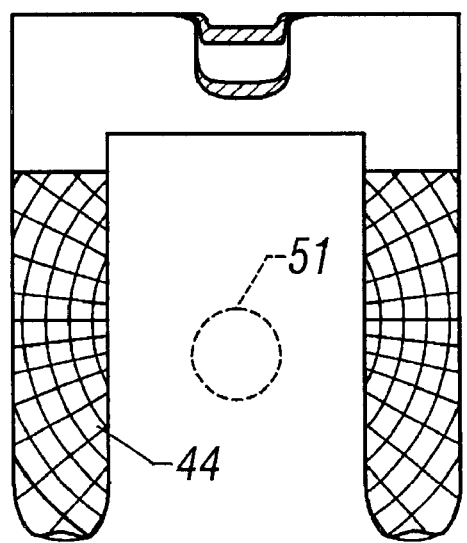
FIG. 8 is a pictorial illustration of the contact surface of the stabilizer showing the textile fibers or threads directionally oriented for improved traction.

As illustrated in FIG. 8, the fibers or threads of the textile material 44 may be oriented about the target segment 51 of the heart, or other organ, to provide optimum friction traction surrounding the target segment 41. Thus, the fibers or threads of the textile material 44 may be oriented substantially in a circular pattern around the target segment 51 to provide enhanced traction against movements of the surface of the heart relative to the target segment 51.

Figure 2A:
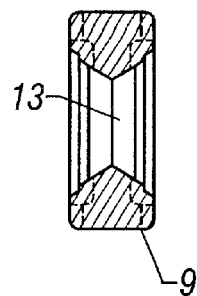
FIG. 2a is a sectional view of a ring with tapered bore from each end forming sockets to receive ball-shaped elements therein.
Figure 2B:
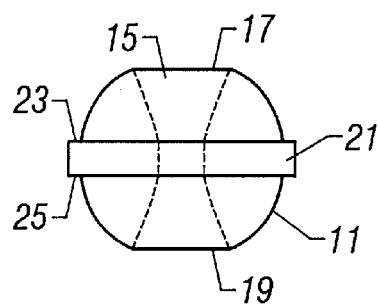
FIG. 2b is a plan view of a ball element having upper and lower hemispherical surfaces separated by a protruding equatorial band, and having an internal bore extending between upper and lower pole regions of the hemispheres.
Figure 3:
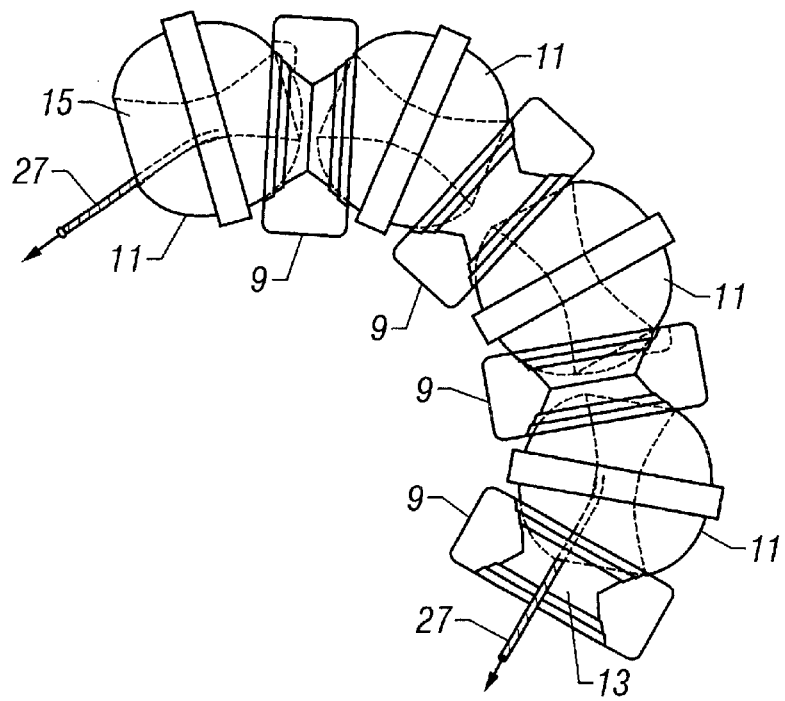
FIG. 3 is a pictorial illustration of a stacked structure of rings and ball elements in alternating succession along the illustrated portion of length, and including a tensioning cable through the internal bores of the rings and ball elements.

Referring now to the pictorial illustrations of FIGS. 2a and 2b, there are shown, respectively, a side sectional view of a ring 9, and plan view of a ball element 11 according to the present invention for iterative stacking in alternating sequence, as shown in FIG. 3, to form one embodiment of a support structure for the stabilizing element 45 of the present invention. It should be noted that other supporting structures can be used with the present invention (See, for example, U.S. Pat. Nos. 5,782,746; 5,749,892; 5,894,843). The ring 9 is substantially cylindrical with an axial bore 13 therethrough that tapers inwardly from each end either in continuous manner or in stepped manner as shown to form a socket for receiving therein the spherical surface of an adjacent ball element 11. Stepped taper provides multiple ring-oriented points of contact with the spherical surface of a mating ball element 11, as shown in FIG. 3, to obviate the need for closely-mating interior surface matched to the spherical surface of the ball element 11.

The ball element 11 also includes an internal bore 15 therethrough along the polar axis which tapers inwardly from the frusto-spherical planar ends 17, 19 formed where the internal bore intersects the external spherical surfaces at upper and lower polar locations. In addition, the ball element 11 includes a protruding equatorial band 21 that protrudes radially outwardly from the spherical surface to form radially-extending shoulders 23, 25 with each of the upper and lower hemispherical surfaces. The ball element 11 and the ring 9 may each be formed of substantially bioinert materials such as stainless steel or polymer materials that are relatively rigid to provide firm seating of one hemispherical surface of a ball element 11 within the bore of an adjacent ring 9, as shown in FIG. 3. Alternatively, at least the rings 9 may be formed of a resilient polymer material such as polyurethane silicone, or thermoplastic elastomer to promote non-slip engagement of ball elements 11 and rings 9 and to accommodate any slightly mismatched mating surfaces thereon by slight conformal deformation of the tapered internal bore 13 of a ring 9.

Referring now to FIG. 3, there is shown an alternate, iterative stacking of mating ball elements 11 and rings 9 to produce an articulatable structure of selected overall length dimension based upon the numbers of rings 9 and ball elements 11 that are iteratively stacked together in the manner as shown. The shoulders 23, 25 formed at the equatorial band 21 on each ball element 11 are disposed to abut adjacent rings 9 and serve as a stop against further angular rotation of a ball element 11 relative to an adjacent ring 9. In addition, the stacked structure includes a flexible cable 27 passing through the internal bores 13, 15 of the stacked rings 9 and ball elements 11 to facilitate selectively compressing the stacked structure between ends in the manner as later described herein. The cable terminates in a lateral bar 29 at the distal end of the stacked structure, as shown in FIGS. 1 and 4, and in a tensioning screw 31 at the proximal end of the stacked structure. A yoke-like member 32 forms the last element at the distal end of the stacked structure, with either a mating tapered internal bore for mating with an adjacent ball element, or a semi-spherical end for mating with an adjacent ring, and also includes a lateral groove 33 at the distal end substantially aligned with the lateral bar 29 attached to the distal end of the cable 27. At the proximal end of the stacked structure, a housing 35 may include a tapered internal bore for mating with an adjacent ball element 11, or a semi-spherical end for mating with an adjacent ring 9. The housing 35 supports a tensioning screw 31 at the end of cable 27 in threaded engagement with a rotatable thumbnut 39. Thus, rotating the thumbnut 39 tightens the cable 27 within the stacked structure to compress the rings 9 and ball elements 11 together into rigid, seated engagement over the length of the stacked structure. Clamp 37 is affixed to the housing 35 and is adjustable over a substantial range to facilitate clamping onto conventional forms of retractors commonly used in thoracic and cardiac surgery to maintain open the surgical site near the sternum or between ribs and overlaying the heart. Thus, the stacked structure selectively made rigid by tightening thumbscrew 39 may rigidly support an attachment to the distal end element 32 relative to such common rib-spreading frame or retractor to which the housing 35 may be clamped 37.

Figure 5:
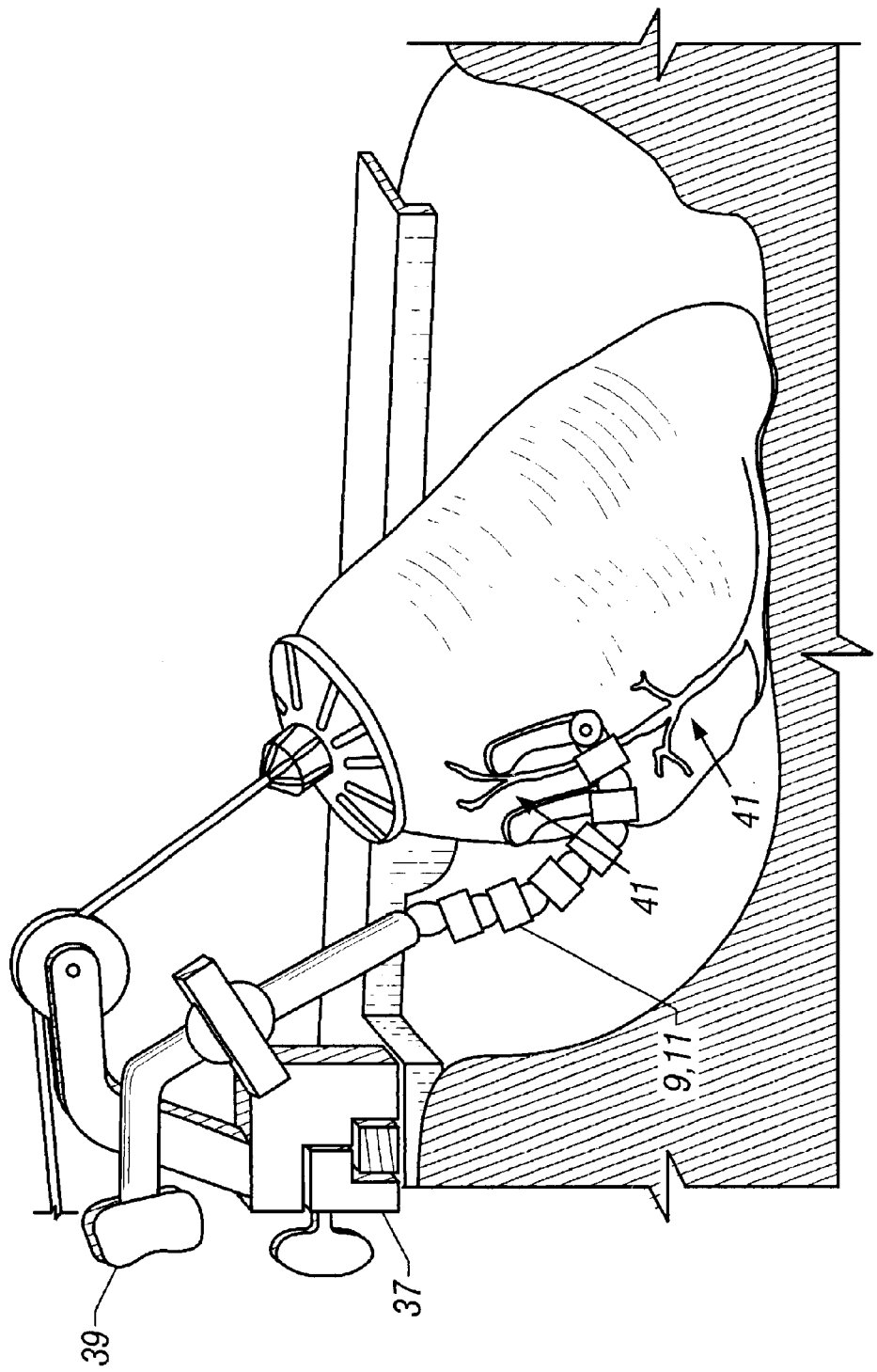
FIG. 5 is a partial pictorial illustration of the supporting element positioned on a heart.
Figure 6:
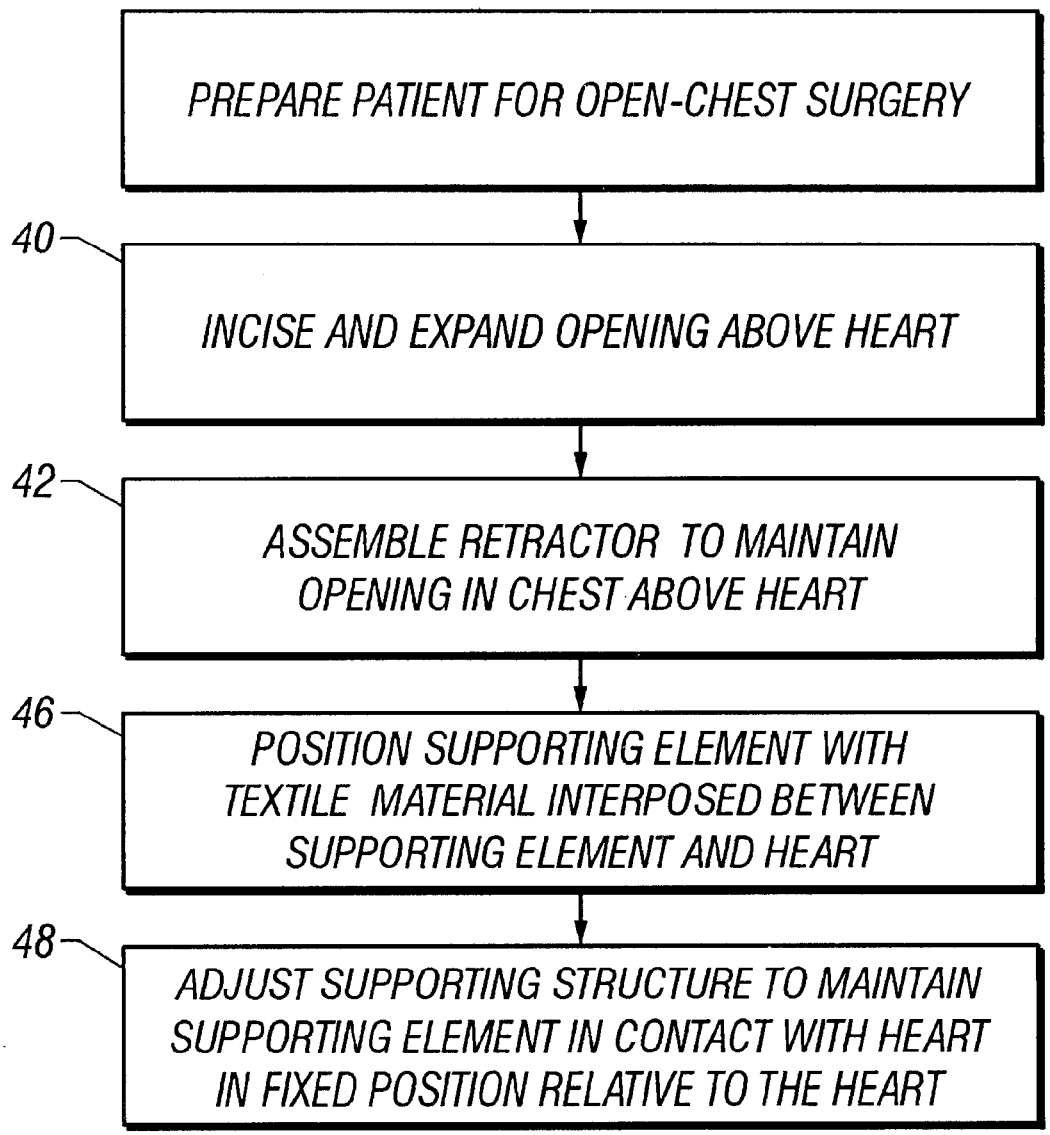
FIG. 6 is a flow chart illustrating the operating sequence for stabilizing a beating heart in accordance with one embodiment of the present invention.

With reference now to FIG. 6 the flow chart illustrates the method for use on a patient in supine position undergoing cardiac or cardiovascular surgical procedure through an opening prepared 40 in the patient's rib cage (e.g., via a thoracotomy or sternotomy, or the like). The fork-like element 41 of the stacked structure may be manipulated into position beneath the heart or other organ that may be manipulated into surgical position by a strap, or vacuum or sutured manipulator, as illustrated in FIG. 5. The clamp 37 may then be clamped onto a conventional frame or retractor commonly used to spread and retain ribs separated 42 about the surgical opening into the patient's chest, and the tines 43 of the supporting element 41, may then be positioned 46 with the textile material 44 in surface contact with a selected segment of the beating heart. The thumbnut 39 may then be rotated to tighten the cable 27 and thereby firmly position 48 the element 41 in contact with the heart by rigidifying the stacked structure 9, 11 in the manner as previously described herein relative to the supporting frame or retractor. Alternatively, the clamp 37 may be affixed to the surgical frame that is commonly used to maintain a surgical opening through the patient's rib cage in a sequence different than as described above, ultimately to provide stabilizing support for the beating heart at the distal end of the rigidified structure relative to the supporting frame. With the cylindrical element 45 also positioned within the groove 33 of the distal end element 32 as the lateral bar 29 tightens the cylindrical element 45 into the groove 33, the tines 43 are then firmly positioned beneath the heart, as illustrated in FIG. 5, to stabilize at least a target segment of the surfaces of the beating heart in contact with the tines 43. Of course, other organs such as liver, pancreas, spleen, kidney, and the like, may also be conveniently supported or stabilized in selected surgical position using the present apparatus. And, other shapes than protruding tines 43, such as flat paddle or spoon-like elements may be substituted for the fork-like element 41 of FIG. 1, and may be formed of bioinert and rigid material such as stainless steel or polycarbonate, or the like.

In another embodiment, the supporting element 41 may include a pair of spaced tines 43 that protrude in substantially coplanar array and that are covered with a layer of foamed material 50 such as polyurethane foam which, in turn, is covered by a layer of textile material 44. The foam material may be absorbent to promote dry surface contact of the textile material 44 with the moist surface of an organ such as a heart. Additionally, as illustrated in FIG. 8, fibers, or threads, of the textile material 44 may be oriented in substantially circular array above a central target region 51 at which a surgical procedure on an organ is to be performed. In this way, the textile material 44 in contact with an organ may provide enhanced traction against movements of the organ relative to the target region 51.

In operation, the stacked structure of rings 9 and ball elements 11 between housing 35 at the proximal end and the textile-covered supporting element 41 at the distal end remains in flexible and conformable configuration while cable 27 is slack. In this configuration, the supporting element 41 may be rotated and angularly manipulated into position in contact with the heart, or other organ of a patient while loosely coupled to the stacked structure in flexible configuration. The clamp 37 may be positioned on a retractor or otherwise firmly positioned in substantially fixed position relative to a patient's heart, as illustrated in FIG. 5, and the thumbnut 39 may then be turned relative to the screw end 31 of cable 27 to tension the cable 27 between the ends thereof. The cable 27 in tension compresses the supporting element 41, the lateral bar 29, the grooved distal end element 32, the stacked assembly of rings 9 and ball elements 11, and housing 35 into a rigid structure that thereby rigidly supports the heart, or other organ, relative to the frame or reference member to which the clamp 37 on housing 35 is affixed. Of course, unscrewing thumbnut 39 relative to the screw end 31 of cable 27 slackens the cable 27 and relaxes the stacked structure into flexible configuration to facilitate convenient repositioning or removal of the structure.

Therefore, the stabilizer and surgical method for use on the heart or other organ according to the present invention provide enhanced slip-free contact with the heart of a surgical patient, and diminishes the incidence of contact trauma on the surface of the heart being stabilized against relative movement by the stacked structure that can be selectively manipulated between flexible and rigid configurations.

What is claimed is:

1. Organ stabilizing apparatus comprising:

contact members disposed for contacting an organ and including a layer of textile material including fibers oriented in a substantially circular pattern within a plane of the contact members on a surface of the contacting members disposed for positioning adjacent the organ.

2. Organ stabilizing apparatus comprising:

a contact member disposed for contacting an organ and including a layer of textile material on a surface of the contacting member disposed for positioning adjacent the organ; and a layer of compliant foam material interposed between the contact member and the textile material.

3. Apparatus according to claim 2 in which the foam material is absorbent.

4. Organ stabilizing apparatus comprising:

a contact member including a pair of spaced tines in substantially co-planar orientation disposed for contacting an organ and including a layer of foam material interposed between each tine and textile material on a surface of the contacting member disposed for positioning adjacent the organ.

* * * * *